United States Patent [19]

Wakselman et al.

[11] Patent Number: 4,731,450

[45] Date of Patent: Mar. 15, 1988

[54] PROCESS FOR PERFLUOROALKYLATION OF AROMATIC DERIVATIVES

[75] Inventors: Claude Wakselman, Paris; Marc Tordeux, Sceaux, both of France

[73] Assignee: Rhone-Poulenc Specialites Chimiques, France

[21] Appl. No.: 865,346

[22] Filed: May 21, 1986

[30] Foreign Application Priority Data

May 22, 1985 [FR] France ........................... 85 07695
Oct. 25, 1985 [FR] France ........................... 85 15857

[51] Int. Cl.$^4$ ................... C07D 213/26; C07C 21/18; C07C 43/02; C07C 43/03; C07C 69/76; C07C 69/773

[52] U.S. Cl. ................................. 546/303; 546/346; 570/124; 570/127; 570/128; 570/129; 570/130; 570/132; 560/83; 560/100; 560/103; 562/480; 562/490; 562/492; 562/493; 564/152; 564/153; 564/155; 564/161; 564/180; 564/183; 568/56; 568/57; 568/630; 568/655; 568/579; 568/765; 568/775; 568/631; 568/634; 568/639; 558/425

[58] Field of Search ................ 546/303, 346; 570/124, 570/127, 128, 129, 130, 132; 560/83, 100, 103; 562/480, 490, 492, 493; 564/152, 153, 155, 161, 180, 183; 568/56, 57, 630, 655, 579, 765, 775, 631, 634, 639; 558/425

[56] References Cited

FOREIGN PATENT DOCUMENTS 0008453  8/1979  European Pat. Off. ............ 546/346
114359  12/1983  European Pat. Off. ............ 546/346

OTHER PUBLICATIONS

J. Fluorine Chem., 1983, 22, 541.

*Primary Examiner*—Henry R. Jiles
*Assistant Examiner*—J. Richter
*Attorney, Agent, or Firm*—Finnegan, Henderson, Farabow, Garrett & Dunner

[57] ABSTRACT

A process for the perfluoroalkylation of aromatic derivatives. In a first stage, an aromatic derivative, sulfur dioxide and a metal selected from the group consisting of zinc, aluminum, manganese, cadmium, magnesium, tin, iron, nickel and cobalt, are brought into contact in a solvent, preferably a polar aprotic solvent. In a second stage, a perfluoroalkyl bromide or iodide is added to react with the aromatic derivative.

20 Claims, No Drawings

PROCESS FOR PERFLUOROALKYLATION OF AROMATIC DERIVATIVES

The present invention relates to a process for perfluoroalkylation of aromatic derivatives. More particularly, it relates to a process for perfluoroalkylation of aromatic derivatives by means of perfluoroalkyl halides.

According to J. Fuchikami and I. Ojima (J. Fluorine Chemistry 1983, 22, 541) it is known to perfluorinate aromatic amines or phenols using perfluoroalkyl iodides or bromides whose alkyl chain contains at least three carbon atoms in the presence of metallic copper as a catalyst. Trifluoromethylation of para-chloroaniline with trifluoromethyl iodide produces only traces of trifluoromethyl-para-chloroaniline. Since trifluoromethyl iodide is not industrially available, and since the reaction yield is very low, this method cannot be converted to an industrial scale. Trifluoromethylation of phenols and of their derivatives has not been described.

It is also known, according to European Pat. No. 114,359, to perfluoroalkylate aromatic derivatives, and especially anisole (Example 9) using a long-chain perfluoroalkyl iodide, for 30 hours at 170° C. and in the presence of a ruthenium-based catalyst. Trifluoromethylation is not described anywhere in this patent, as in the preceding paper. Since trifluoromethyl iodide is not made industrially, this perfluoroalkylation method cannot be envisaged.

No methods for perfluoroalkylation of aromatic derivatives are described in any process of the prior art. The traditional perfluoroalkylation processes, such as those described in European Pat. No. 8,453 cannot be applied to phenols, because perfluoroalkylation of the hydroxyl group, and not of the aromatic nucleus, takes place in this case.

The present invention overcomes these technical problems and relates to a process of perfluoroalkylation of aromatic derivatives comprising the steps of bringing an aromatic derivative into contact with sulfur dioxide and a metal selected from the group consisting of zinc, aluminum, manganese, cadmium, iron, magnesium, tin, cobalt and nickel in a solvent, preferably a polar aprotic solvent; and then adding a perfluoroalkyl bromide or iodide, if appropriate, mixed with sulfur dioxide to react with the aromatic derivative.

Preferred aromatic derivatives correspond to the formula (I):

Ar—R)$_n$   (I)

wherein:
  Ar denotes a mono- or polycyclic aromatic or heterocyclic radical;
  R denotes at least one substituent selected from the group consisting of hydrogen, chlorine, bromine, saturated or unsaturated, unsubstituted or substituted, linear, branched or cyclic alkyl radicals, ether, substituted or unsubstituted alkoxy, substituted or unsubstituted aryl, aryloxy, alkylthio, arylthio, amino, hydroxy, carboxylate, acyloxy, ester, amido, nitrile and acid radicals; and
  n is an integer equal to 1, 2, or 3.

It is preferable to use aromatic derivatives of the formula (I) in which Ar denotes a monocyclic aromatic radical and R$_1$ denotes at least one substituent selected from the group consisting of amino and hydroxy radicals.

Representative aromatic derivatives of formula (I) which can be used in the process of the present invention include benzene, toluene, meta-xylene, phenyl oxide, biphenyl, bromobenzene, chlorobenzene, alpha-chlorotoluene, benzyl alcohol, ethyl phenylacetate, pyridine, 2-methylpyridine, amines such as, in particular, aniline, methylanilines, phenoxyanilines, phenylanilines, chloroanilines, methoxyanilines, aminonaphthalene, diaminobenzenes, 3-aminopyridine, phenolic derivatives, among which may be mentioned phenols, cresols, phenylphenols, chlorophenols, aminophenols, anisoles, methoxyphenols, dihydroxybenzenes, 4-tert-butylphenol, 3-tert-butylphenol, and 2-hydroxypyridine.

According to the process of the invention, the perfluoroalkyl bromide or iodide preferably corresponds to the following general formula (II)

$$C_nF(2n+1)X \qquad (II)$$

wherein
  n is an integer from 1 to 12; and
  X denotes Br or I.

From an economic standpoint it is preferable to use trifluoromethyl bromide when n is equal to 1 and perfluoroalkyl iodides when n is greater than 1.

Trifluoromethyl bromide is a firefighting gas (M. R. C. Gerstenberger and A. Haas, Angew. Chem. Int. Ed. 1981, 20, 647), which is an industrial product manufactured on a large scale. Hence, trifluoromethyl bromide is readily accessible to industry so far as cost is concerned.

Since trifluoromethyl iodide is not made industrially, it is available only at a price which makes it completely unusable. On the other hand, as soon as the alkyl chain contains at least two atoms, perfluoroalkyl iodides are to be found on the market at prices which are well below those of their bromo homologs.

Among the metals, it is preferable to choose those which have only one oxidation state, and more particularly those whose oxidation-reduction potential in a basic medium is between −0.8 and −2 volts.

Thus, zinc, aluminum, manganese and cadmium are particularly preferred.

Among the latter, it is advantageous to choose zinc, for reasons of economy.

The metal is advantageously employed in a dispersed form to ensure optimum contact with the gases used in the process of the invention. The shape and size of the metal particles will be adapted by one skilled in the art to the reactivity of the products employed.

The solvent chosen should, as far as possible, allow sulfur dioxide and the perfluoroalkyl halide to dissolve. Polar aprotic solvents meet this requirement, and, among these, the following are preferred:
acetonitrile
dimethylformamide (DMF)
dimethylacetamide (DMA)
hexamethylphosphoramide (HMPA)
N-methylpyrrolidone (NMP) and
dimethyl sulfoxide (DMSO).

Still more preferably, dimethylformamide and dimethyl sulfoxide are employed.

To enable the process to be used more rapidly, it is preferable to add an organic and/or inorganic base during the first stage, i.e., the step where an aromatic derivative is brought into contact with sulfur dioxide and the metal in a solvent. Sodium hydroxide, potassium hydroxide, lime and alkali metal metabisulfites may be particularly mentioned among the inorganic bases. It is preferable to use sodium metabisulfite.

Among the organic bases, it is preferable to employ pyridines and, more preferably pyridine and methylpyridines.

According to a highly favored embodiment of the invention, a molar ratio of metal to the aromatic derivative of from 0.05 to 1, preferably from 0.10 to 0.20, is used, and a molar ratio of perfluoroalkyl halide to the aromatic derivative preferably greater than or equal to 1 is used. When excess perfluoroalkyl halide is used and when the halide used is trifluoromethyl bromide, the latter can be readily recycled because it exists in a gaseous state.

The molar ratio of sulfur dioxide to the aromatic derivative employed is preferably from 0.05 to 1.5.

When an inorganic base is employed, it is preferable to use it in a molar ratio of inorganic base to the aromatic derivative of from 0.4 to 1 and when a pyridine is employed, it is preferable to use it in a molar ratio of pyridine to the aromatic derivative of from 0.5 to 1.5.

The temperature at which the reaction is carried out is preferably from $-20°$ C. to $115°$ C. and, still more preferably, from $0°$ to $90°$ C.

It is advantageous to employ a pressure of from 1 to 10 bars. However, an appropriate pressure can readily be selected by one skilled in the art based on the particular reactants used.

The operation is preferably carried out in the absence of oxygen.

Products obtained using the process of the present invention include trifluoromethylbenzene, trifluoromethyltoluenes, dimethyltrifluoromethylbenzenes, trifluoromethylphenoxybenzenes, trifluoromethylbiphenyls, bromotrifluoromethylbenzenes, chlorotrifluoromethylbenzenes, trifluoromethyl(chloromethyl)benzenes, trifluoromethylbenzyl alcohols, ethyl (trifluoromethylphenyl)acetate, trifluoromethylpyridines, methyltrifluoromethylpyridines, trifluoromethylanilines, methyl-, methoxy-, chloro-, phenyl- and phenoxytrifluoromethylanilines, diaminotrifluoromethylbenzenes, diaminobistrifluoromethylbenzenes, trifluoromethyl-N,N-diethyl-anilines, pentafluoroethylanilines, perfluorobutylanilines, aminotrifluoromethylpyridines, trifluoromethylphenols, chlorotrifluoromethylphenols, methyltrifluoromethylphenols, methoxytrifluoromethylphenols, aminotrifluoromethylphenols, tert-butyltrifluoromethylphenols and hydroxytrifluoromethylpyridines.

The products provided by the process of the present invention are used especially as synthesis intermediates in the pharmaceutical or plant-protection industry.

The invention will be described more completely with the aid of the following examples which should not be considered as limiting the invention.

EXAMPLE 1

The following were introduced into a thick glass apparatus:
40 g of benzene
100 ml of dimethylformamide
40 ml of 2-methylpyridine
5 g of zinc and 20 g of sodium metabisulfite.

The apparatus was evacuated and then maintained by a thermostat at $65°$ C.

20 g of sulfur dioxide were added. The mixture was stirred for 3 hours under a bromotrifluoromethane pressure which was maintained at from 7 to 8 atmospheres. After filtration, the apparatus was subsequently opened, and the reaction mixture was poured into 200 g of ice and 60 ml of concentrated hydrochloric acid. The mixture was extracted with ether.

After removal of the solvents and distillation, 12.7 g of trifluoromethyl benzene (17% yield) were obtained. delta$_F$ = $-64$ ppm, b.p. $102°$ C.

EXAMPLE 2

The method of Example 1 was repeated and the following reactants were added:
40 g of toluene
100 ml of dimethylformamide
40 ml of 2-methylpyridine
5 g of zinc, and
20 g of sodium metabisulfite.
20 g of sulfur dioxide were added.

After 3 hours' reaction and ether extraction, the following were obtained by distillation and identified by gas phase chromatography:
15.3 g of trifluoromethyltoluenes (b.p. $145°$ C.)
  i.e. 9% of 2-trifluoromethyltoluene, delta$_F$ $-60.6$ ppm delta$_H$ 2.47 ppm (3H, q, J:1 Hz) 7.24 ppm (2H, m) 7.4 ppm (1H, t, J:7.5 Hz) 7.6 ppm (d, J:7.5 Hz),
  4% of 3-trifluoromethyltoluene delta$_F$ $-61.6$ ppm delta$_H$ 2.41 ppm (3H, s) 7.45 ppm (2H, m) 7.35 ppm (2H, m),
  9% of 4-trifluoromethyltoluene, delta$_F$ $-61.8$ ppm delta$_H$ 2.4 ppm (3H, s) 7.25 ppm (2H, d, J:8.1 Hz) 7.5 ppm (2H, d) and
1.5 g of 6-trifluoromethyl-2-methylpyridine (2% yield) delta$_F$ $-68$ ppm
  delta$_H$ 2.64 ppm (3H, s) 7.3 ppm (1H, d) 7.46 ppm (1H, d) 7.73 ppm (1H, t, J:7.75 Hz).

EXAMPLE 3

The method of Example 1 was repeated with benzene replaced by 40 g of meta-xylene.

After 3 hours' reaction and ether extraction, the following were obtained after distillation of xylene and identification using gas phase chromatography:
(1) 1,3-dimethyl-5-trifluoromethylbenzene
  delta$_F$ $-61.3$ ppm (s) delta$_H$ 2.37 ppm (6H, s) 7.27 ppm (3H)
(2) 2,4-dimethyl-1-trifluoromethylbenzene;
  yield: 5%
  delta$_F$ $-60.3$ ppm (broad s) delta$_H$ 2.3 ppm (3H,s) 2.43 ppm (3H, broad s) 7 ppm (2H, m) 7.53 ppm (1H, m)
(3) 1,3-dimethyl-2-trifluoromethylbenzene
  delta$_F$ $-53$ ppm (sept., d, J:3.5 Hz)
  delta$_H$ 2.5 ppm (q, J:3.5 Hz) 7.13 ppm (3H, m).

EXAMPLE 4

10 g of biphenyl oxide, 25 ml of dimethylformamide, 10 ml of 2-methylpyridine, 1 g of zinc and 8 g of sodium metabisulfite were introduced into a thick glass flask. The flask was evacuated. It was then placed in a thermostat at $60°$ C. 4 g of sulfur dioxide were added and the flask was shaken for 3 hours under a bromotrifluoromethane pressure which was maintained at from 2.5 to 3.7 atmospheres. The flask was then opened. 50 g of ice and 15 ml of concentrated hydrochloric acid were added. The mixture was extracted with ether, the ether phase rinsed with dilute hydrochloric acid and a solution of sodium chloride, and then dried with magnesium sulfate. Distillation and chromatography detected:
(1) 8% of 3-trifluoromethylphenoxybenzene
    $delta_F$ −62 ppm $delta_H$ 7.5 6.8 ppm (m)
(2) 11% of 2-trifluoromethylphenoxybenzene
    $delta_F$ −60.9 ppm $delta_H$ 7.65 ppm (1H d, J:8.3 Hz) 6.91 ppm (1H, d, J:8.4 Hz) 7.44−7 ppm (7H, m)
(3) 11% of 4-trifluoromethylphenoxybenzene
    $delta_F$ −61 ppm $delta_H$ 7.54 ppm (2H, d) 7.02 ppm (2H, d, J:8.7 Hz) 7.44−7 ppm (5H, m).

EXAMPLE 5

The method of Example 1 was repeated but benzene was replaced by 40 g of biphenyl.

After 3 hours' reaction, ether extraction and sublimation at 40° C., 14 g of a mixture of 3-trifluoromethylbiphenyls were obtained; an 18% yield (m.p.: 45° C.) $delta_F$ −56.7 ppm 17%; $delta_F$ −62.3 ppm 28%, $delta_F$ −62.2 ppm 55%

EXAMPLE 6

The method of Example 1 was repeated, with benzene replaced by 40 g of bromobenzene.

After 3 hours' reaction, the following were obtained after ether extraction and identification by gas phase chromatography:
3% 2-bromotrifluoromethylbenzene
   $delta_F$ −61.8 ppm
1% 3-bromotrifluoromethylbenzene
   $delta_F$ −61.7 ppm
3% 4-chlorotrifluoromethylbenzene
   $delta_F$ −61.8 ppm.

EXAMPLE 7

The method of Example 1 was repeated, with benzene being replaced by 40 g of chlorobenzene.

·After 3 hours' reaction, the following were obtained after ether extraction and identification by gas phase chromatography:
3% 2-chlorotrifluoromethylbenzene
   $delta_F$ −62.4 ppm
1% 3-chlorotrifluoromethylbenzene
   $delta_F$ −61.7 ppm
3% 4-chlorotrifluoromethylbenzene
   $delta_F$ −61.8 ppm.

EXAMPLE 8

The method of Example 1 was repeated but benzene was replaced by 40 g of alpha-chlorotoluene.

After 3 hours' reaction, the following were obtained after ether extraction and identification by gas phase chromatography:
3% 2-trifluoromethylchloromethylbenzene
   $delta_F$ −57 ppm
6% 3-trifluoromethylchloromethylbenzene
   $delta_F$ −61.6 ppm 6% 4-trifluoromethylchloromethylbenzene
   $delta_F$ −61.8 ppm.

EXAMPLE 9

The method of Example 1 was repeated but benzene was replaced by 40 g of benzyl alcohol.

After 3 hours' reaction, the following were obtained after ether extraction and identification by gas phase chromatography:
6% 2-trifluoromethylbenzyl alcohol
   $delta_F$ −60 ppm
6% 3-trifluoromethylbenzyl alcohol
   $delta_F$ −61.6 ppm
6% 4-trifluoromethylbenzyl alcohol
   $delta_F$ −61.7 ppm.

EXAMPLE 10

The method of Example 1 was repeated but benzene was replaced by 40 g of ethyl phenylacetate.

After 3 hours' reaction, the following were obtained after ether extraction and identification by gas phase chromatography:
3% ethyl (2-trifluoromethylphenyl)acetate
   $delta_F$ −59.3 ppm
6% ethyl (3-trifluoromethylphenyl)acetate
   $delta_F$ −61.6 ppm
6% ethyl (4-trifluoromethylphenyl)acetate
   $delta_F$ −61.8 ppm.

EXAMPLE 11

The method of Example 1 was repeated but benzene was replaced by 50 g of pyridine without 2-methylpyridine.

After 3 hours' reaction, distillation yielded:
3% 3-trifluoromethylpyridine
   $delta_F$ −61.7 ppm
   b.p. 108°–110° C.
1% 4-trifluoromethylpyridine
   $delta_F$ −64.2 ppm
   b.p. 110°–113° C.
5% 2-trifluoromethylpyridine
   $delta_F$ −67.7 ppm
   b.p. 140° C.

EXAMPLE 12

Example 1 was repeated but no benzene was present.

After 3 hours' reaction, the following were obtained by ether extraction:
(1) 2-methyl-4-trifluoromethylpyridine; yield 1%
    $delta_F$ −63.8 ppm $delta_H$ 2.67 ppm (3H, s) 7.36 ppm (1H, d) 7.45 ppm (1H) 8.77 ppm (1H, d, J:5.5 Hz)
(2) 2-methyl-3-trifluoromethylpyridine; yield 4%
    $delta_F$ −62.2 ppm (broad s) $delta_H$ 2.89 ppm (3 H, broad s) 7.29 ppm (1H, d, J:8 Hz) 7.84 ppm (1H, d×d) 8.62 ppm (1H, d, J:4.75 Hz)
(3) 2-methyl-5-trifluoromethylpyridine; yield 3%
    $delta_F$ −62 ppm (s) $delta_H$ 2.62 ppm (3H, s) 7.86 ppm (1H) 8.2 ppm (1H, d, J:8 Hz) 8.77 ppm (1H, d)
(4) 2-methyl-6-trifluoromethylpyridine; yield 2%
    $delta_F$ −68 ppm (s) $delta_H$ 2.63 ppm (3H, s) 7.4 ppm (1H, d, J:7.7 Hz) 7.52 ppm (1H, d, 7.7 Hz) 7.84 ppm (1H, t).

EXAMPLE 13

10 g (0.11 mole) of aniline, 25 ml of dimethylformamide and 1 g of zinc were introduced into a thick glass flask.

The flask was placed in a Parr apparatus.

The flask was evacuated. 8 g of sulfur dioxide were added. The flask was shaken for 3 hours at a bromotrifluoromethane pressure which was maintained at from 2.4 to 3.7 atmospheres. The reaction was exothermic. The flask was then opened. 50 g of ice and 15 ml of concentrated hydrochloric acid were added. The mixture was extracted with ether. Distillation yielded:
(1) 3.4 g of 2-trifluoromethylaniline (20% yield)
    $delta_F$ = −63 ppm; b.p. 14 mm Hg 66° C.
(2) 1.7 g of 4-trifluoromethylaniline (10% yield)
    $delta_F$ = −60 ppm; b.p. 14 mm Hg 86° C.

EXAMPLE 14

The method of Example 13 was repeated, with the introduction of:
10 g (0.11 mole) of aniline
25 ml of dimethylformamide
1 g of zinc
10 ml of 2-methylpyridine, and
6 g of powdered sodium hydroxide After 3 hours' reaction and ether extraction, distillation yielded:
4.8 g of 2-trifluoromethylaniline (28% yield)
2.6 g of 4-trifluoromethylaniline (15% yield).

EXAMPLE 15

The method of Example 14 was repeated, with sodium hydroxide replaced by 10 g of powdered sodium metabisulfite.

After 2 hours' reaction and ether extraction, the following were obtained:
6.2 g of 2-trifluoromethylaniline (36% yield)
3.4 g of 4-trifluoromethylaniline (20% yield).

EXAMPLE 16

The method of Example 13 was repeated, with the introduction of:
10 g (0.093 mole) of 2-methylaniline
25 ml of dimethylformamide
1 g of zinc, and
10 ml of 2-methylpyridine.

After 3 hours' reaction and ether extraction, 4.5 g of a mixture were obtained and separated by gas phase chromatography, yielding:
2-methyl-6-trifluoromethylaniline (15% yield)
  $delta_F$: −62 ppm $delta_H$: 7.33 ppm (t, 2H) 6.73 ppm (t, 1H) J=8.5 Hz
2-methyl-4-trifluoromethylaniline (15% yield)
  $delta_F$ −60 ppm $delta_H$: 7.33 ppm (m, 2H) 6.73 ppm (d, 1H) J =8.5Hz

EXAMPLE 17

The method of Example 16 was repeated with 2-methylaniline replaced by 10 g of 4-methylaniline, and 2-methylpyridine replaced by 10 ml of 2,6-dimethylpyridine.

After 3 hours' reaction, 4.9 g (0.028 mole) of 4-methyl-2-trifluoromethylaniline were obtained (30% yield).
B.p.: 41°/0.5 mm Hg
$delta_F$: −63 ppm $delta_H$: 6.7 ppm (1H); 7.03 ppm (1H); J:8.5 Hz, 7.3 ppm (1H).

EXAMPLE 18

The method of Example 16 was repeated with 2-methylaniline replaced by 10 g of 3-methoxyaniline (0.08 mole).

After 3 hours' reaction, the following were obtained:
0.8 g of 2,6-bistrifluoromethyl-3-methoxyaniline (4% yield)
  $delta_F$: −53.3 ppm; −60.8 ppm
  $delta_H$: 7.53 ppm (d); 6.37 ppm (d) J=8.5 Hz 3.87 ppm (3H, s)
3.3 g of 3-methoxy-2-trifluoromethylaniline (21% yield)
  $delta_F$: 53.2 ppm
3.7 g of 5-methoxy-2-trifluoromethylaniline (24% yield)
  $delta_F$: −60.6 ppm
3.7 g of 3-methoxy-4-trifluoromethylaniline (24% yield)
  $delta_F$: −60 ppm.

EXAMPLE 19

The method of Example 16 was repeated with 2-methylaniline replaced by 10 g of 2-chloroaniline (0.08 mole) and with the flask set by a thermostat at 50° C.

After 4 hours' reaction, the following were obtained:
1 g of 2-chlorobistrifluoromethylaniline (5% yield)
3.2 g of 2-chloro-6-trifluoromethylaniline (21% yield)
  $delta_F$: −62 ppm
3.2 g of 2-chloro-4-trifluoromethylaniline (21% yield)
  $delta_F$: −60 ppm

EXAMPLE 20

The method of Example 19 was repeated, with 2-chloroaniline replaced by 10 g of 3-chloroaniline (0.08 mole).

After 3 hours' reaction, the following were obtained:
2.3 g of 5-chloro-2-trifluoromethylaniline (15% yield)
  $delta_F$: −62 ppm $delta_H$=−6.73 ppm (2H, m); 7.27 ppm (1H, s)
1.8 g of 3-chloro-2-trifluoromethylaniline (12% yield)
  $delta_F$: −54 ppm
2.1 g of 3-chloro-4-trifluoromethylaniline (14% yield)
  $delta_F$: −60 ppm.

EXAMPLE 21

The method of Example 14 was repeated with aniline replaced by 10 g of 4-phenylaniline (0.05 mole) and with 2-methylpyridine replaced by 10 ml of 2,6-dimethylpyridine.

After 3 hours' reaction 1.55 g of 4-phenyl-2-trifluoromethylaniline were obtained (11% yield)
  $delta_F$: −62 ppm.

EXAMPLE 22

The method of Example 21 was repeated with 4-phenylaniline replaced by 10 g of 4-phenoxyaniline (0.053 mole).

After 3 hours' reaction,
2.2 g of 4-phenoxy-2-trifluoromethylaniline were obtained (16% yield)
  $delta_F$: −63 ppm.

EXAMPLE 23

The method of Example 21 was repeated with 4-phenylaniline replaced by 10 g of 1-aminonaphthalene (0.07 mole).

After 3 hours' reaction, the following mixture was obtained:
1-amino-2-trifluoromethylnaphthalene (30% yield)
  $delta_F$: 62 ppm
1-amino-4-trifluoromethylnaphthalene (20% yield)
  $delta_F$: −59 ppm.

EXAMPLE 24

The method of Example 16 was repeated with 2-methylaniline replaced by 10 g of 1,2-diaminobenzene.

After 3 hours' reaction, the following were obtained:
0.9 g of 2,3-diamino-1,4-bistrifluoromethylbenzene (4% yield)
  $delta_F$: −61.6 ppm (s); $delta_H$: 6.97 ppm (s)
0.7 g of 1,2-diamino-3,4-bistrifluoromethylbenzene (3% yield)
  $delta_F$: −55.2 ppm; $delta_H$: 7.15 ppm (1H, d); $JH_{H-H}$=8.5 Hz
1.6 g of 1,2-diamino-3-trifluoromethylbenzene (10% yield)
  $delta_F$: −62 ppm 4.4 g of 1,2-diamino-4-trifluoromethylbenzene (27% yield)
delta$_F$: −61 ppm.

EXAMPLE 25

The method of Example 24 was repeated with 1,2-diaminobenzene replaced by 10 g of 1,3-diaminobenzene.
After 3 hours' reaction, the following were obtained:
1.6 g of 1,3-diamino-2,4-bistrifluoromethylbenzene (7% yield)
1.4 g of 1,5-diamino-2,4-bistrifluoromethylbenzene (6% yield)
2.6 g of 1,3-diamino-2-trifluoromethylbenzene (16% yield)
1.1 g of 1,3-diamino-4-trifluoromethylbenzene (7% yield).

EXAMPLE 26

The method of Example 21 was repeated with 4-phenylaniline replaced by 10 g of 1,3-diaminobenzene (0.092 mole).
After 2 hours' reaction, the following were obtained:
3.8 g of 1,3-diamino-2,4-bistrifluoromethylbenzene (17% yield)
  delta$_F$: −54 ppm; −60.5 ppm delta$_H$: 7.25 ppm; 5.98 ppm; J HH=8.25 Hz
1.6 g of 1,5-diamino-2,4-bistrifluoromethylbenzene (7% yield)
  delta$_F$: −60.7 ppm; delta$_H$: 7.5 ppm, 5.95 ppm
0.5 g of 1,3-diamino-2-trifluoromethylbenzene (3% yield) delta$_F$: −54 ppm
1.3 g of 1,3-diamino-4-trifluoromethylbenzene (8% yield) delta$_F$: −61.2 ppm.

EXAMPLE 27

The method of Example 16 was repeated with 2-methylaniline replaced by 10 g of N,N-diethylaniline, and 2-methylpyridine replaced by pyridine.
After 3 hours' reaction 5.3 g (36% yield) of an equimolar mixture of the following were obtained:
2-trifluoromethyl-N,N-diethylaniline
  delta$_F$=−58 ppm
4-trifluoromethyl-N,N-diethylaniline
  delta$_F$: −60 ppm.

EXAMPLE 28

The method of Example 14 was repeated with bromotrifluoromethane replaced by 30 g of iodopentafluoroethane. The pressure dropped below atmospheric pressure.
After 3 hours' reaction 3.1 g of an equimolar mixture of the following were obtained:
2-pentafluoroethylaniline (14% yield)
  delta$_F$: −84 ppm (3F); −113 ppm (2F)
4-pentafluoroethylaniline
  delta$_F$: −85 ppm (3F); −113.6 ppm (2F).

EXAMPLE 29

10 g of aniline, 25 ml of dimethylformamide, 1 g of zinc, 10 ml of 2,6-dimethylpyridine and 6 g of powdered sodium hydroxide were introduced into a conical flask. The atmosphere in the conical flask consisted of a 50/50 mixture of argon and sulfur dioxide. 35 g of perfluorobutyl iodide were added with stirring while the temperature was maintained at 10° C. 50 g of ice and 15 ml of concentrated hydrochloric acid were then added. The mixture was extracted with ether, and 20 g of an equimolar mixture (60% yield) of the following were obtained:
2-perfluorobutylaniline
  delta$_F$: −82 ppm (3F) −111 ppm −124 ppm −127 ppm
4-perfluorobutylaniline
  delta$_F$: −82 ppm (3F) −111 ppm −124 ppm −127 ppm.

EXAMPLE 30

The method of Example 13 was repeated with zinc replaced by 1 g of cadmium.
After 3 hours' reaction and ether extraction, the following were obtained:
(1) 3.1 g of 2-trifluoromethylaniline (18% yield)
(2) 1.4 g of 4-trifluoromethylaniline (8% yield).

EXAMPLE 31

The method of Example 13 was repeated with zinc replaced by 1 g of iron.
After 3 hours' reaction and ether extraction, the following were obtained:
(1) 1 g of 2-trifluoromethylaniline (6% yield)
(2) 0.5 g of 4-trifluoromethylaniline (3% yield).

EXAMPLE 32

The method of Example 13 was repeated with zinc replaced by 1 g of manganese.
After 3 hours' reaction and ether extraction, the following were obtained:
(1) 0.9 g of 2-trifluoromethylaniline (5% yield)
(2) 0.4 g of 4-trifluoromethylaniline (2% yield).

EXAMPLE 33

40 g of aniline, 100 ml of dimethylformamide, 40 ml of 2-methylpyridine and 4 g of zinc were introduced into a thick glass apparatus. The apparatus was held by a thermostat at 20° C. It was evacuated and then 20 g of sulfur dioxide were added. The mixture was stirred for 2 hours at a bromotrifluoromethane pressure which was maintained from 6.5 to 7.5 atmospheres. The reaction was exothermic: the temperature reached 70° C. after a quarter of an hour and then dropped slowly.
The apparatus was then opened. The reaction mixture was poured into 200 g of ice and 60 ml of concentrated hydrochloric acid. The mixture was extracted with ether. Distillation yielded:
(1) 20 g of 2-trifluoromethylaniline (29% yield)
(2) 10 g of 4-trifluoromethylaniline (14% yield).

EXAMPLE 34

The method of Example 13 was repeated and the following were introduced:
10 g (0.093 mole) of 3-methylaniline
25 ml of dimethylformamide
10 ml of 2-methylpyridine
6 g of sodium metabisulfite, and
1 g of zinc.
After 3 hours' reaction and ether extraction, 9.9 g of a mixture were obtained and were separated by gas phase chromatography. This yielded:
(1) 3-methylbistrifluoromethylaniline (4% yield)
(2) 5-methyl-2-trifluoromethylaniline (12% yield)
  delta$_F$: −61 ppm delta$_H$: 7.3 ppm (1H, d, J:8.5 Hz) 6.57 ppm (2H, d) 2.25 ppm (3H, s)
(33-methyl-2-trifluoromethylaniline (18% yield)
  delta$_F$: −53.5 ppm (q) delta$_H$: 7.07 ppm (1H, t, J:8.5 Hz) 6.5 ppm (2H, m) 2.33 ppm (3H, q, J$_{HF}$: 3.3 Hz)

(4) 3-methyl-4-trifluoromethylaniline (18% yield)
delta$_F$: −58 ppm (broad s) delta$_H$: 7.37 ppm (1H, d, J:8.5 Hz) 6.43 ppm (2H, m) 2.33 ppm (3H, broad s).

EXAMPLE 35

The method of Example 13 was repeated and the following were introduced:
10 g of 3-aminopyridine
25 ml of dimethylformamide
6 g of sodium metabisulfite, and
1 g of zinc.

After 3 hours' reaction a mixture of the following was obtained:
(1) 1% of 3-amino-2-trifluoromethylpyridine
delta$_F$: −64.6 ppm; delta$_H$: 7.04 ppm (1H, d, d, J:8.5 Hz 1.5 Hz)
(2) 3% of 5-amino-2-trifluoromethylpyridine
delta$_F$: −64.6 ppm; delta$_H$: 6.93 ppm (1H, d, d, J:8.25 Hz 2.5 Hz) 7.39 ppm (1H, d, J:8.25 Hz) 8.03 ppm (1H, d, J:2.5 Hz).

EXAMPLE 36

The method of Example 4 was repeated with biphenyl oxide replaced by 10 g of phenol.
After 4 hours' reaction, ether extraction yielded:
(1) 3.5 g of 2-trifluoromethylphenol, b.p 147°–148° C. (20% yield)
delta$_F$: −61.6 ppm; delta$_H$: 7.48 ppm (2H, d) 7 ppm (2H, t).

The residue was purified by gas phase chromatography; in addition to unreacted phenol, it contained:
(2) 1.7 g of 4-trifluoromethylphenol (10% yield)
delta$_F$: −60.3 ppm; delta$_H$: 7.53 ppm (2H, d) 6.93 ppm (2H, d, J:8.5 Hz).

EXAMPLE 37

The method of Example 36 was repeated with phenol replaced by 10 g of 3-chlorophenol.
After 4 hours' reaction, the following were obtained:
(1) 2.6 g of 3-chloro-2-trifluoromethylphenol (17% yield)
delta$_F$: −55 ppm; delta$_H$: 7.23 ppm (1H, t, J:8.5 Hz) 6.93 ppm (2H, m)
(2) 2.9 g of 5-chloro-2-trifluoromethylphenol (19% yield)
delta$_F$: −60.3 ppm; delta$_H$: 7.4 ppm (1H, d, J:8.5 Hz) 6.93 ppm (2H, m)
(3) 1.8 g of 3-chloro-4-trifluoromethylphenol (12% yield)
delta$_F$: −62 ppm; delta$_H$: 7.53 ppm (1H, d, J: 8.5 Hz) 6.87 ppm (2H, m)

EXAMPLE 38

The method of Example 36 was repeated with phenol replaced by 10 g of 2-chlorophenol.
After 4 hours' reaction and ether extraction, the following were obtained:
(1) 1.4 g of 6-chloro-2-trifluoromethylphenol (9% yield)
delta$_H$: 7.37 ppm (2H, d) 6.63 ppm (1H, t, J:8.5 Hz)
delta$_F$: −62.6 ppm (s)
(2) 0.9 g of 2-chloro-4-trifluoromethylphenol (6% yield)
delta$_H$: 7.46 ppm (1H, d, J:1 Hz) 7.27 ppm (1H, d×d, J:8.5 Hz; 1 Hz) 6.63 ppm (1H, d, J:8.5 Hz);
delta$_F$: −61 ppm.

EXAMPLE 39

The method of Example 36 was repeated with phenol replaced by 10 g of 3-methylphenol.

After 4 hours' reaction and ether extraction, the following were obtained:
(1) 4.2 g of 3-methyl-2-trifluoromethylphenol (26% yield)
b.p. 23 mm Hg 77°–79° C., delta$_F$: −53.3 ppm (q)
delta$_H$: −7.27 ppm (1H, d×d, J:8 Hz,J:9 Hz); 6.8 ppm (2H, d); 2.43 ppm (3H, q, J$_{HF}$: 3 Hz)
(2) 2.6 g of 5-methyl-2-trifluoromethylphenol (16% yield)
b.p.23 mm Hg 84°–86° C., delta$_F$: −60 ppm
delta$_H$: −7.4 ppm (1H, d, J:8.5 Hz) 6.8 ppm (2H, d) 2.27 ppm (3H, s).
After purification by vapor phase chromatography:
(3) 3.9 g of 3-methyl-4-trifluoromethylphenol (24% yield)
delta$_F$: −59 ppm (broad s); delta$_H$: 7.43 ppm (1H, d, J:8.5 Hz) 6.7 ppm (2H, m) 2.37 ppm (3H, broad s)

EXAMPLE 40

The method of Example 36 was repeated with phenol replaced by 10 g of 3-methoxyphenol.
After 3 hours' reaction and ether extraction, the following were obtained:
(1) 3.9 g of 3-methoxy-2-trifluoromethylphenol (25% yield)
delta$_F$: −53.8 ppm; delta$_H$: 7.33 ppm (1H, t, J: 8.5 Hz) 6.56 ppm (2H, d) 3.87 ppm (3H, s)
(2) 3.9 g of 5-methoxy-2-trifluoromethylphenol (25% yield)
delta$_F$: −59 ppm; delta$_H$: 7.43 ppm (1H, d, J:8.5 Hz) 6.53 ppm (2H, m) 3.77 ppm (3H, s)
(3) 3.9 g of 3-methoxy-4-trifluoromethylphenol (25% yield)
delta$_F$: −61 ppm; delta$_H$: 7.43 ppm (1H, d, J:8.5 Hz) 6.36 ppm (1H, m) 3.83 ppm (3H, s).

EXAMPLE 41

The method of Example 36 was repeated with phenol replaced by 10 g of 1,3-dimethoxybenzene.
After 4 hours' reaction and ether extraction, the following were obtained:
(1) 3.3 g of 2,4-dimethoxytrifluoromethylbenzene (23% yield)
delta$_H$: 7.4 ppm (1H, d, H:8.5 Hz) 6.8 ppm (1H, broad s) 6.45 ppm (1H, m) 3.83 ppm (3H, s) 3.78 ppm (3H, s) delta$_F$: −61.3 ppm (s)
(2) 0.7 g of 2,6-dimethoxytrifluoromethylbenzene (4% yield)
delta$_H$: 7.45 ppm (1H, t) 6.63 ppm (2H, d, J:8.5 Hz) 3.88 ppm (6H, s) delta$_F$: −54 ppm (s)

EXAMPLE 42

10 g of 1,3-dihydroxybenzene, 25 ml of dimethylformamide, 1 g of zinc and 10 ml of 2-methylpyridine were introduced into a thick glass flask.
The flask was placed in a Parr apparatus.
The flask was evacuated; 8 g of sulphur dioxide were added. The flask was shaken for 3 hours at a bromotrifluoromethane pressure which was maintained at from 2.4 to 3.7 atmospheres. The reaction was exothermic. The flask was then opened and 50 g of ice and 15 ml of concentrated hydrochloric acid were added. The mixture was extracted with ether. A mixture of the following was obtained:
(1) 1 g of 1,3-dihydroxy-2-trifluoromethylbenzene (6% yield)
delta$_F$: −53.3 ppm (2) 2.8 g of 1,3-dihydroxy-4-trifluoromethylbenzene (17% yield)
delta$_F$: −58.8 ppm.

EXAMPLE 43

The method of Example 42 was repeated with dihydroxybenzene replaced by 10 g (0.02 mole) of 3-aminophenol.

After 3 hours' reaction and ether extraction, a mixture was obtained and purified by chromatography on silica plates, a 90/10 mixture of benzene and ether acetate were used as eluant:
(1) 0.5 g of bistrifluoromethyl-3-aminophenol (3% yield)
(2) 2.8 g of 3-amino-2-trifluoromethylphenol (17% yield)
delta$_F$: −54.5 ppm, m.p. 121° C.
(3) 2.8 g of 3-amino-4-trifluoromethylphenol (17% yield)
delta$_F$: −61 ppm, m.p. 101° C.
(4) 2.8 g of 5-amino-2-trifluoromethylphenol (17% yield)
delta$_F$: −60.6 ppm, m.p. 131° C.

EXAMPLE 44

The method of Example 43 was repeated with 3-aminophenol replaced by 10 g of 2-aminophenol.

After 3 hours' reaction and ether extraction, the following were obtained:
(1) 2 g of 2-aminobistrifluoromethylphenol (9% yield)
(2) 3.1 g of 2-amino-3-trifluoromethylphenol (19% yield)
delta$_F$: −62 ppm
(3) 4.8 g of 2-amino-5-trifluoromethylphenol (30% yield)
delta$_F$: −59 ppm.

EXAMPLE 45

The method of Example 36 was repeated with bromotrifluoromethane replaced by 40 g of iodopentafluoroethane and with the flask regulated by a thermostat at 20° C.

After 3 hours' reaction and ether extraction, the following were obtained:
(1.35 g of 2-pentafluoroethylphenol (6% yield)
delta$_F$: −83.7 ppm (3F) −111.7 ppm (2F)
(2) 1.6 g of 4-pentafluoroethylphenol (7% yield)
delta$_F$: −84.3 ppm (3F) −113.3 ppm (2F).

EXAMPLE 46

2 g of phenol, 5 ml of dimethylformamide, 2 ml of 2-methylpyridine, 0.2 g of zinc and 1 g of sodium metabisulfite were introduced into a conical flask.

The atmosphere in the conical flask consisted of a 50/50 mixture of argon and sulfur dioxide.

9 g of perfluorohexyl iodide were added with stirring. This was followed by the addition of 10 g of ice and 5 ml of concentrated hydrochloric acid. The mixture was extracted with ether; after purification, the following were obtained:
(1) 1.2 g of 2-perfluorohexylphenol (14% yield)
delta$_F$: −80 ppm (3F) −107 ppm (2F) −121 ppm (6F) −125 ppm (2F)
delta$_H$: 7.36 ppm (2H, d) 7 ppm (2H, t, J:8.5 Hz)
(2) 1.2 g of 4-perfluorohexylphenol (14% yield)
delta$_F$: −80 ppm (3F) −108 ppm (2F) −121 ppm (6F) −125 ppm (2F) delta$_H$ 7.43 ppm (2H, d) 7.03 ppm (2H, d) J:8.5 Hz.

EXAMPLE 47

The method of Example 4 was repeated with biphenyl oxide replaced by 10 g of 4-tert-butylphenol.

After 3 hours' reaction and ether extraction, the following were obtained:
3.6 g of 4-tert-butyl-2-trifluoromethylphenol, m.p. 49° (24% yield)
delta$_F$: −60 ppm; delta$_H$: 7.55 ppm (1H, s broad) 7.33 ppm (1H, d) 6.8 ppm (1H, d, J:8.5 Hz) 1.3 ppm (9H, s).

EXAMPLE 48

The method of Example 4 was repeated with biphenyl oxide replaced by 10 g of 3-tert-butylphenol.

After 3 hours' reaction and ether extraction, the following were obtained:
(1) 0.4 g of 3-tert-butyl-2-trifluoromethylphenol (3% yield)
delta$_F$: −50.2 ppm
(2) 0.6 g of 3-tert-butyl-4-trifluoromethylphenol (4% yield)
delta$_F$: −50.5 ppm
(3) 2.8 g of 5-tert-butyl-2-trifluoromethylphenol (19% yield)
delta$_F$: −61.3 ppm.

EXAMPLE 49

The method of Example 4 was repeated with biphenyl oxide replaced by 10 g of 2-hydroxypyridine.

After 3 hours' reaction and ether extraction, the following were obtained:
(1) 3.4 g of 2-hydroxy-6-trifluoromethylpyridine, m.p. 52° C. (20% yield)
delta$_F$: −65.3 ppm; delta$_H$: 7.93 ppm (1H, broad d, J: 7 Hz) 7.63 ppm (1H, broad d, J:7 Hz) 6.37 ppm (1H, t).

What is claimed is:

1. A process for the preparation of perfluoroalkylated aromatic derivatives comprising the steps of bringing an aromatic derivative, sulfur dioxide, and a metal selected from the group consisting of zinc, aluminum, manganese, cadmium, iron, magnesium, tin, nickel and cobalt into contact in a solvent; and then adding a perfluoroalkyl bromide or iodide to react with said aromatic derivative.

2. The process of claim 1, wherein said solvent is a polar aprotic solvent.

3. The process of claim 1, wherein the aromatic derivative corresponds to the formula (I):

Ar—R)$_n$      (I)

wherein:
Ar denotes a mono- or polycyclic or heterocyclic aromatic radical,
R denotes at least one substituent selected from the group consisting of hydrogen, chlorine, bromine, saturated or unsaturated, unsubstituted or substituted, linear, branched or cyclic alkyl radicals, ether, substituted or unsubstituted alkoxy, substituted or unsubstituted aryl, aryloxy, alkyltio, arylthio, amino, hydroxy, carboxylate, acyloxy, ester, amido, nitrile and acid radicals; and
n is an integer equal to 1, 2 or 3.

4. The process of claim 3, wherein, in the formula (I) Ar denotes a monocyclic aromatic radical; and R denotes an amino or hydroxy radical.

5. The process of claim 1, wherein the perfluoroalkyl bromide or iodide corresponds to the formula (II)

$$C_nF_{(2n+1)}X \quad (II)$$

wherein:
n is an integer from 1 to 12; and
X denotes Br or I.

6. The process of claim 5, wherein, in the formula (II), when n is equal to 1, X denotes bromine.

7. The process of claim 5, wherein, in the formula (II), when n is greater than 1, X denotes iodine.

8. The process of claim 1, wherein the metal is zinc.

9. The process of claim 2, wherein the polar aprotic solvent is selected from the group consisting of dimethylformamide, dimethyl sulfoxide, acetonitrile, hexamethylphosphoramide, dimethylacetamide and N-methylpyrrolidone.

10. The process of claim 1, wherein at least one compound selected from the group consisting of an inorganic base and a pyridine is brought into contact with said aromatic derivative prior to said step of adding said bromide or iodide.

11. The process of claim 10, wherein a pyridine, unsubstituted or substituted by at least one methyl group, is brought into contact with said aromatic derivative prior to said step of adding said bromide or iodide.

12. The process of claim 10, wherein said inorganic base is sodium metabisulfite.

13. The process of claim 1, wherein the molar ratio of the metal to the aromatic derivative is from 0.05 to 1.

14. The process of claim 13, wherein said molar ratio is from 0.10 to 0.20.

15. The process of claim 1, wherein the molar ratio of the perfluoroalkyl halide to the aromatic derivative is greater than or equal to 1.

16. The process of claim 1, wherein the molar ratio of sulfur dioxide to the aromatic derivative is from 0.05 to 1.5.

17. The process of claim 10, wherein the molar ratio of the inorganic base to the aromatic derivative is from 0.4 to 1.

18. The process of claim 10, wherein the molar ratio of the pyridine to the aromatic derivative is from 0.5 to 1.5.

19. The process of claim 1, wherein the temperature at which the reaction is carried out is from $-20°$ C. to $115°$.

20. The process of claim 19, wherein said temperature is from $0°$ to $90°$ C.

* * * * *